United States Patent
Gallagher

(10) Patent No.: US 10,433,927 B2
(45) Date of Patent: Oct. 8, 2019

(54) HINGED LONG SEALED TRAY AND METHOD

(71) Applicant: Medtronic Vascular, Inc., Santa Barbara, CA (US)

(72) Inventor: John Gallagher, Galway (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 0 days.

(21) Appl. No.: 15/333,287

(22) Filed: Oct. 25, 2016

(65) Prior Publication Data

US 2018/0110578 A1     Apr. 26, 2018

(51) Int. Cl.
    *A61B 50/33*           (2016.01)
    *A61M 25/00*         (2006.01)
    *A61B 50/30*           (2016.01)
    *A61B 50/00*           (2016.01)

(52) U.S. Cl.
CPC .............. *A61B 50/33* (2016.02); *A61B 50/30* (2016.02); *A61M 25/002* (2013.01); *A61B 2050/0065* (2016.02); *A61B 2050/3011* (2016.02)

(58) Field of Classification Search
CPC . A61B 50/30; A61B 50/33; A61B 2050/0065; A61B 2050/3008; B65D 43/162; B65D 75/366; B65D 2575/366; B65D 2575/368
USPC .. 206/363, 387.13, 438, 461, 467, 470–471; 220/4.23–4.24, 835, 837; 16/225, 227, 16/319, 366, DIG. 13
See application file for complete search history.

(56) References Cited

U.S. PATENT DOCUMENTS

| | | | | |
|---|---|---|---|---|
| 2,026,311 A | * | 12/1935 | Harris ................. | C21D 9/0025 220/682 |
| 2,145,481 A | * | 1/1939 | Harvey ................ | A47G 21/001 206/822 |
| 3,351,270 A | * | 11/1967 | Hohnjec ............. | B65D 43/162 16/225 |
| 3,616,487 A | * | 11/1971 | Dearth ................ | E05D 1/02 16/225 |
| 3,629,901 A | * | 12/1971 | Wolf .................. | E05D 1/02 16/227 |
| 3,967,730 A | * | 7/1976 | Driscoll .............. | B65D 75/368 206/268 |
| 4,005,776 A | * | 2/1977 | Seeley ................ | B65D 75/366 206/306 |

(Continued)

OTHER PUBLICATIONS

U.S. Appl. No. 62/359,049, of Jeffrey Barnell, titled "Hybrid Sealed Tray for Long Catheter Delivery Systems", filed Jul. 6, 2016.

(Continued)

*Primary Examiner* — Chun Hoi Cheung
*Assistant Examiner* — Brijesh V. Patel

(57) ABSTRACT

A packaging assembly comprising an outer tray and a lid coupled to the outer tray. The lid and the outer tray define a sterile cavity therein. The packaging assembly further includes an inner tray housing a delivery system within the sterile cavity. The outer tray includes a proximal portion, a distal portion, and a hinged portion coupling the proximal portion to the distal portion. To aseptically present the inner tray for removal from the outer tray, the lid is partially or completely removed. The proximal portion is then bent downward to expose the inner tray for removal.

20 Claims, 5 Drawing Sheets

(56) References Cited

U.S. PATENT DOCUMENTS

| | | | | |
|---|---|---|---|---|
| 4,057,932 A * | 11/1977 | Spencer | A01G 9/104 | 206/423 |
| 4,106,621 A * | 8/1978 | Sorenson | A61M 5/002 | 206/365 |
| D265,387 S * | 7/1982 | Nattrass | D11/156 | |
| 4,593,816 A * | 6/1986 | Langenbeck | B65D 25/06 | 206/425 |
| 4,609,113 A * | 9/1986 | Seki | B65D 1/265 | 215/382 |
| 4,938,462 A * | 7/1990 | Gould | B65D 75/366 | 206/470 |
| 4,966,283 A * | 10/1990 | Sykes | B29C 51/00 | 206/311 |
| 5,012,578 A * | 5/1991 | Siefer | B26B 29/00 | 30/47 |
| 5,048,707 A * | 9/1991 | Hallberg | A21B 3/133 | 220/324 |
| 5,082,112 A * | 1/1992 | Dunklee | A61B 1/00142 | 206/363 |
| D336,373 S * | 6/1993 | Crawford | D4/199 | |
| D338,123 S * | 8/1993 | Crawford | D4/199 | |
| 5,244,089 A * | 9/1993 | Yang | B65D 85/24 | 206/361 |
| 5,379,895 A * | 1/1995 | Foslien | A61B 50/30 | 206/363 |
| 5,405,005 A * | 4/1995 | White | A61F 2/0095 | 206/363 |
| 5,503,294 A * | 4/1996 | Taylor | B65D 1/22 | 220/558 |
| 5,772,031 A * | 6/1998 | Landis | A61B 50/30 | 206/363 |
| 6,010,462 A * | 1/2000 | Stoermer, III | B65B 9/042 | 206/210 |
| 6,070,723 A * | 6/2000 | Lewis | B65D 75/322 | 206/335 |
| 6,533,116 B1 * | 3/2003 | Riley | A61M 25/002 | 206/363 |
| 6,666,348 B2 * | 12/2003 | Fore | B65D 1/26 | 220/315 |
| D561,020 S * | 2/2008 | Kessell | D9/425 | |
| D577,994 S * | 10/2008 | Kessell | D9/425 | |
| 7,685,677 B2 * | 3/2010 | Garg | B65D 43/162 | 16/225 |
| D630,504 S * | 1/2011 | Scott | D9/425 | |
| 8,328,043 B2 * | 12/2012 | Kessell | B65D 1/40 | 220/6 |
| D800,990 S * | 10/2017 | Clements | D1/123 | |
| 2005/0033430 A1 * | 2/2005 | Powers | A61B 17/7059 | 623/17.11 |
| 2005/0085834 A1 * | 4/2005 | Carranza | A61B 50/30 | 606/153 |
| 2006/0266754 A1 * | 11/2006 | Carmona | A47J 47/02 | 220/666 |
| 2007/0017921 A1 * | 1/2007 | Carmona | A47J 47/02 | 220/666 |
| 2007/0074990 A1 * | 4/2007 | Merboth | A01N 1/02 | 206/438 |
| 2012/0000920 A1 * | 1/2012 | Anhalt | B65D 1/22 | 220/608 |
| 2012/0305441 A1 | 12/2012 | Murray et al. | | |
| 2013/0056387 A1 * | 3/2013 | Numata | A61M 25/002 | 206/557 |
| 2013/0168400 A1 * | 7/2013 | Kessell | B65D 1/40 | 220/666 |
| 2016/0159528 A1 * | 6/2016 | Kessell | B65D 1/40 | 206/277 |

OTHER PUBLICATIONS

U.S. Appl. No. 15/277,509, of Jeffrey Barnell, titled "Hybrid Sealed Tray for Long Catheter Delivery Systems", filed Sep. 27, 2016.
U.S. Appl. No. 15/277,537, of Jeffrey Barnell, titled "Biomatter Capture Mechanism and Method", filed Sep. 27, 2016.
U.S. Appl. No. 15/332,968, of Jeffrey Barnell et al., titled "Device Retention Mechanism and Method", filed Oct. 24, 2016.
U.S. Appl. No. 15/333,317, of John Gallagher et al., titled "Slip Card for Long Sealed Trays and Method", filed Oct. 25, 2016.

* cited by examiner

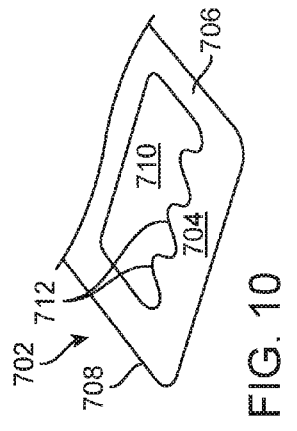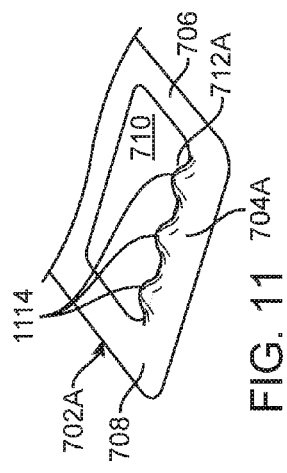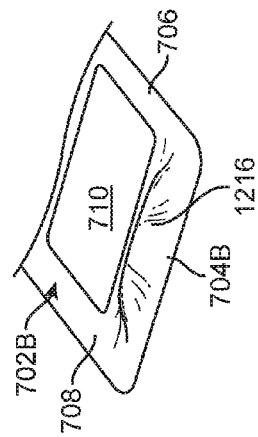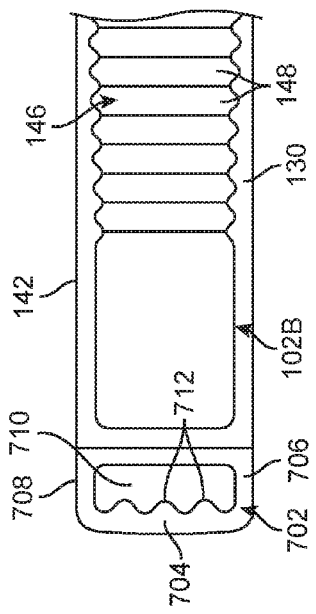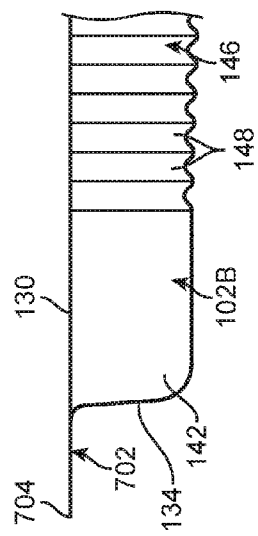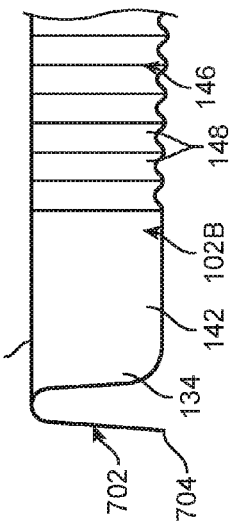

HINGED LONG SEALED TRAY AND METHOD

BACKGROUND

Field

The present application relates to packaging for an intra-vascular device and method. More particularly, the present application relates to packaging for a device for treatment of intra-vascular diseases and related methods.

Description of the Related Art

Long catheter delivery systems, e.g., one meter or greater in length, present challenges in sterile removal and aseptic presentation from the delivery system package. Specifically, the delivery system must be removed from the delivery system package without contacting non-sterile surfaces of the delivery system package.

SUMMARY

A packaging assembly includes an outer tray and a lid coupled to the outer tray. The lid and the outer tray define a sterile cavity therein. The packaging assembly further includes an inner tray housing a delivery system within the sterile cavity. The outer tray includes a proximal portion, a distal portion, and a hinged portion coupling the proximal portion to the distal portion. To aseptically present the inner tray for removal from the outer tray, the lid is partially or completely removed. The proximal portion of the outer tray is then bent downward to expose the inner tray for removal.

These and other features in accordance with various embodiments will be more readily apparent from the detailed description set forth below taken in conjunction with the accompanying drawings.

BRIEF DESCRIPTION OF DRAWINGS

FIG. 7 is a top plan view of an outer tray having a grip in accordance with one embodiment.

FIG. 8 is a side plan view of the outer tray including the grip of FIG. 7 in accordance with one embodiment.

FIG. 9 is a side plan view of the outer tray including the grip of FIG. 7 in a compact position in accordance with one embodiment.

FIG. 10 is a perspective view of the grip of FIG. 7 in accordance with one embodiment.

FIG. 11 is a perspective view of a grip of an outer tray of a catheter delivery system package in accordance with another embodiment.

FIG. 12 is a perspective view of a grip of an outer tray of a catheter delivery system package in accordance with yet another embodiment.

Common reference numerals are used throughout the drawings and detailed description to indicate like elements.

DETAILED DESCRIPTION

Figure 1:
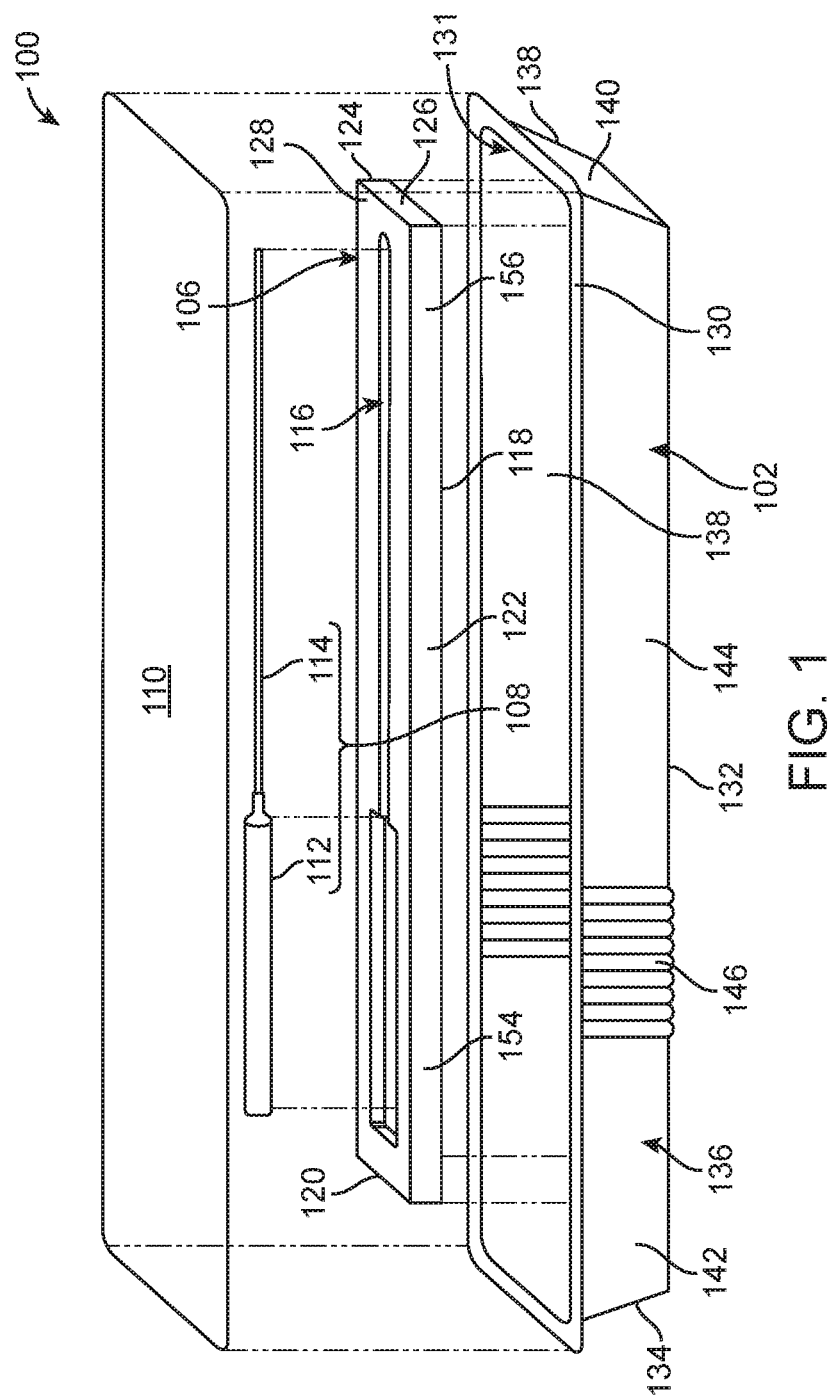
FIG. 1 is an exploded perspective view of a catheter delivery system package in accordance with one embodiment.

FIG. 1 is an exploded perspective view of a catheter delivery system package 100 in accordance with one embodiment. Referring to FIG. 1, catheter delivery system package 100 includes an outer tray 102, an inner tray 106, a delivery system 108, and a lid 110. Catheter delivery system package 100 is a sterile container package for delivery system 108. Delivery system 108 include a handle 112 and a protruding portion 114 protruding from handle 112. Examples of delivery system 108 includes the Valiant™ Aortic Stent Graft System, the Micra™ Transcatheter Pacing System (TPS), and the EnVeoR delivery system, although other delivery systems are used in other embodiments. In one embodiment, delivery system 108 is relatively long, e.g., 1 meter or greater in length.

In one embodiment, delivery system 108, e.g., a medical device, includes one or more stents, grafts, stent-grafts, or other endoluminal devices for delivery and implantation within a patient. Protruding portion 114, e.g., a delivery system catheter, is cylindrical in accordance with one embodiment and is configured to be inserted into a patient. Protruding portion 114 is not limited to a cylindrical member and can take various shapes and have various features in accordance with other embodiments.

Inner tray 106 includes a delivery system opening 116 therein into which delivery system 108 is contained. Generally, delivery system opening 116 is complementary in shape to delivery system 108. In one embodiment, inner tray 106 includes various delivery system holding features for holding delivery system 108. For example, delivery system 108 is press fit into delivery system opening 116, which provides a variable interference fit for holding delivery system 108. In one embodiment, delivery system 108 is snapped into delivery system opening 116 and held therein.

Inner tray 106 is a ridged tray in accordance with one embodiment. Inner tray 106 includes a bottom 118, a proximal end 120, sides 122, 124, a distal end 126, and a top 128. Sides 122, 124 and ends 120, 126 extend upward and away from bottom 118 to top 128. Sides 122, 124 extend opposite one another and between proximal end 120 and distal end 126. Similarly, proximal end 120 and distal end 126 extend opposite one another and between sides 122, 124. Delivery system opening 116 is formed in top 128 in this embodiment. Outer tray 102 and inner tray 106 are generally rectangular in this embodiment although have other shapes in other embodiments.

Outer tray 102 includes an integral lid sealing flange 130 for sealing with lid 110. Outer tray 102 contains inner tray 106 and delivery system 108 therein. In various embodiments, outer tray 102 is formed using injection molding, blow molding, or thermoformed. After inner tray 106 and delivery system 108 are placed in outer tray 102, the sterile barrier is created with the additional of lid 110, e.g., a sealed Tyvek or other film lid. Lid 110 is mounted to lid sealing flange 130. Lid 110 in combination with outer tray 102 define a sterile cavity 131 into which inner tray 106 and delivery system 108 are contained.

Outer tray 102 includes a bottom surface 132, a proximal end 134, sides 136, 138, and a distal end 140. Sides 136, 138 and ends 134, 140 extend upward and away from bottom surface 132 to lid sealing flange 130. Sides 136, 138 extend opposite one another and between proximal end 134 and distal end 140. Similarly, proximal end 134 and distal end 140 extend opposite one another and between sides 136, 138.

As used herein, the distal end of delivery system 108 is identified as the end that is farthest from the operator (handle 112) while the proximal end of delivery system 108 is the end nearest the operator (handle 112). As used herein, the distal end of catheter delivery system package 100 including outer tray 102 and inner tray 106 is identified to the end that is farthest from handle 112 while the proximal end of catheter delivery system package 100 including outer tray 102 and inner tray 106 is the end nearest handle 112. Further, although various features may be referred to as top, bottom, and having other orientations, the features are relative to one another and are not gravitationally orientated. In addition, although various features may be referred to as planar, parallel, or perpendicular, the features may not exactly planar, parallel, or perpendicular, but only substantially planar, parallel, or perpendicular.

Outer tray 102 includes a proximal portion 142, a distal portion 144, and a hinged portion 146 connecting proximal portion 142 to distal portion 144. Lid sealing flange 130 is continuous and extends across proximal portion 142, hinged portion 146, and distal portion 144. Hinged portion 146 is flexible, sometimes called a flexible region, whereas proximal portion 142 and distal portion 144 are rigid, sometimes called rigid regions.

Figure 2:
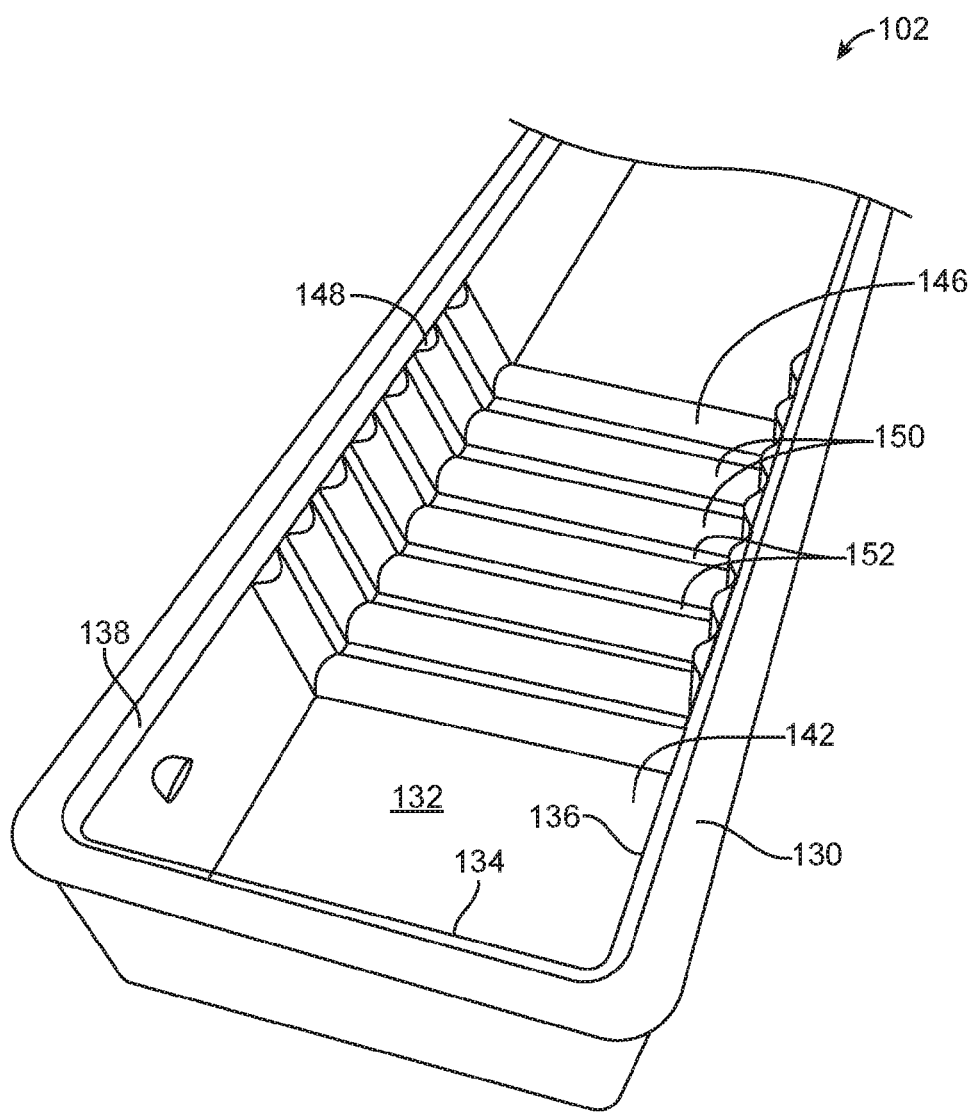
FIG. 2 is a top perspective view of an outer tray of the catheter delivery system package of FIG. 1 in accordance with one embodiment.

FIG. 2 is a top perspective view of outer tray 102 of catheter delivery system package 100 of FIG. 1 in accordance with one embodiment. Referring now to FIGS. 1 and 2 together, hinged portion 146 comprises a plurality of corrugations 148. Corrugations 148 are wrinkles, folds, or ribs that are flexible. In one embodiment, corrugations 148 include an alternative series of parallel ridges 150 and furrows 152. Corrugations 148 are formed in sides 136, 138, and bottom surface 132 in accordance with this embodiment. Corrugations 148 extend from lid sealing flange 130, down side 136, across bottom surface 132, and up side 138 to lid sealing flange 130. Corrugations 148 are perpendicular to the length of outer tray 102 in this embodiment.

Inner tray 106 including delivery system 108 are placed within outer tray 102. More particularly, bottom 118, proximal end 120, sides 122, 124, and distal end 126 of inner tray 106 are adjacent bottom surface 132, proximal end 134, sides 136, 138, and distal end 140 of outer tray 102, respectively. A proximal portion 154 of inner tray 106 lies within proximal portion 142 of outer tray 102. A distal portion 156 of inner tray 106 lies within distal portion 144 of outer tray 102.

Figure 3:
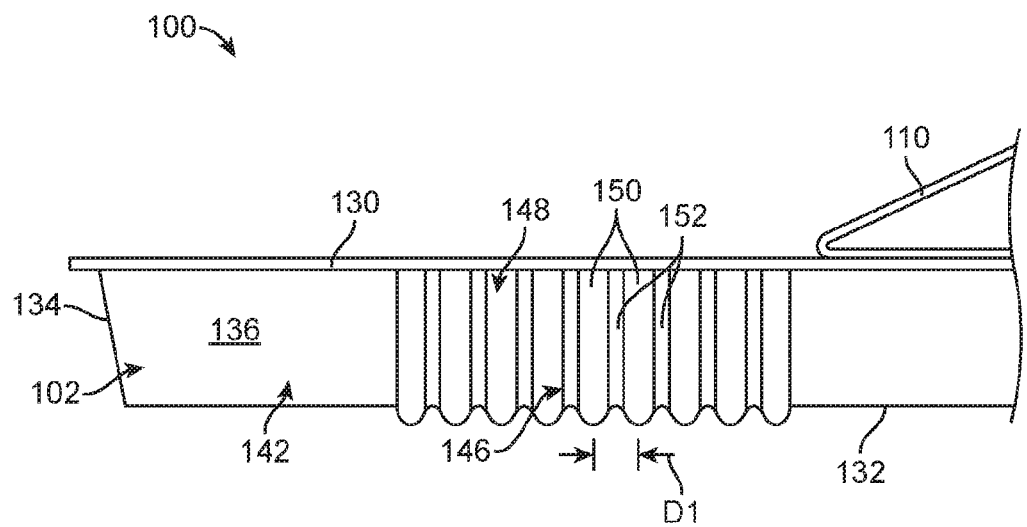
FIG. 3 is a side plan view of the catheter delivery system package of FIG. 1 during removal of an inner tray from the outer tray in accordance with one embodiment.

FIG. 3 is a side plan view of catheter delivery system package 100 of FIG. 1 during removal of inner tray 106 from outer tray 102 in accordance with one embodiment. Referring to FIGS. 1, 2, and 3 together, to remove inner tray 106 including delivery system 108, the circulating nurse or other staff member partially or completely removes lid 110, e.g., by pulling and peeling lid 110 from outer tray 102. This exposes inner tray 106, e.g., proximal portion 154 thereof.

Figure 4:
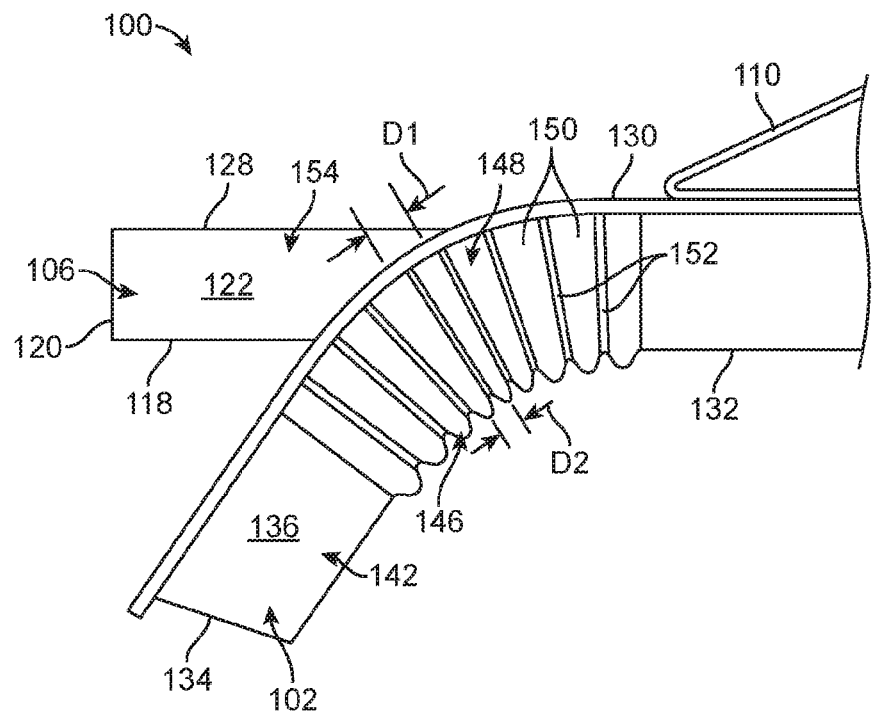
FIG. 4 is a perspective view of the catheter delivery system package of FIG. 3 at a later stage during removal of the inner tray including a delivery system in accordance with one embodiment.

FIG. 4 is a perspective view of catheter delivery system package 100 of FIG. 3 at a later stage during removal of inner tray 106 including delivery system 108 in accordance with one embodiment. As shown in FIG. 4, after partial or complete removal of lid 110 by the circulating nurse or other (non-sterile) user, proximal portion 142 of outer tray 102 is bent from distal portion 144 of outer tray 102 by the circulating nurse or other user. More particularly, hinged portion 146 is deformed to bend proximal portion 142 from distal portion 144 of outer tray 102.

In one embodiment, corrugations 148 are compressed to bend proximal portion 142 from distal portion 144. For example, corrugations 148 have a relatively uniform spacing D1, e.g., between ridges 150 and/or furrows 152, as shown in FIG. 3 in the undeformed state. Corrugations 148 are compressed to have a smaller spacing D2 at bottom surface 132 when in the deformed and bent state as shown in FIG. 4. However, the spacing D1 of corrugations 148 at lid sealing flange 130 remains substantially the same even in the deformed state as shown in FIG. 4. Accordingly, proximal portion 142 is hinged, sometimes called bent, downward from lid sealing flange 130 in a direction away from lid sealing flange 130 and towards bottom surface 132.

This exposes inner tray 106 and delivery system 108 from outer tray 102. More particularly, proximal portion 142 of outer tray 102 is moved away from proximal portion 154 of inner tray 106. This exposes proximal portion 154 of inner tray 106.

This presents inner tray 106 for sterile removal, sometimes called aseptic presentation, from outer tray 102. Lid sealing flange 130 is considered a non-sterile surface in accordance one embodiment and thus contact between inner tray 106 and lid sealing flange 130 must be prevented. To complete removal of inner tray 106 including delivery system 108, inner tray 106 is grasped by the scrub nurse or other staff member in the sterile field and inner tray 106 including delivery system 108 is removed from outer tray 102. Specifically, inner tray 106 is slid out of outer tray 102 including removal of distal portion 156 of inner tray 106 from distal portion 144 of outer tray 102. Delivery system 108 is then removed from inner tray 106 by the scrub nurse or other staff member in the sterile field.

Figure 5:
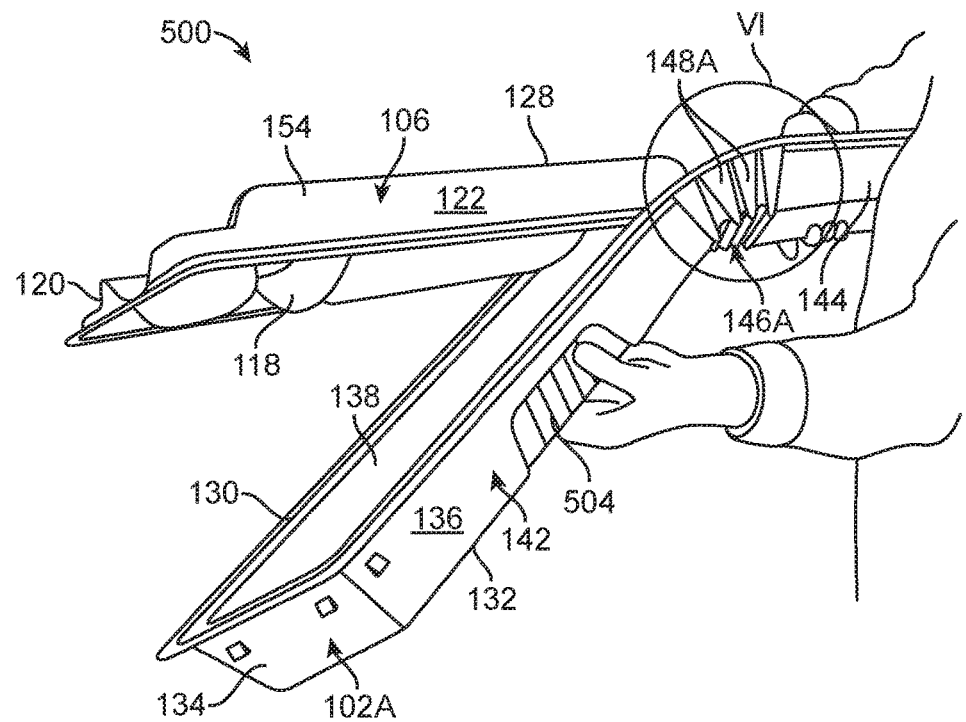
FIG. 5 is a perspective view of a catheter delivery system package during removal of an inner tray in accordance with another embodiment.
Figure 6:
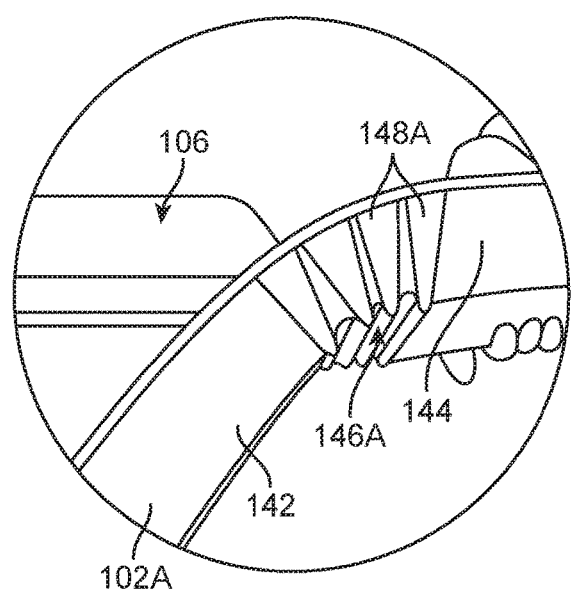
FIG. 6 is an enlarged perspective view of a region VI of the catheter delivery system package of FIG. 5 in accordance with one embodiment.

FIG. 5 is a perspective view of a catheter delivery system package 500 during removal of inner tray 106 in accordance with another embodiment. FIG. 6 is an enlarged perspective view of a region VI of catheter delivery system package 500 of FIG. 5 in accordance with one embodiment. Catheter delivery system package 500 of FIG. 5 is similar to catheter delivery system package 100 of FIGS. 1-4 and only the significant differences are discussed below.

In accordance with this embodiment, an outer tray 102A includes a hinged portion 146A includes triangular shaped corrugations 148A. Further, outer tray 102A includes a grip 504. Grip 504 is an area where the circulating nurse or other user can grip proximal portion 142 and bend proximal portion 142 downward.

In accordance with this embodiment, grip 504 is formed in sides 136, 138 of proximal portion 142 of outer tray 102. Illustrative, grip 504 includes protrusions or other features to assist in grasping of proximal portion 142.

Although a particular grip 504 is illustrated in FIG. 5, a grip can be formed in a variety of locations and shapes on outer tray 102A to facilitate bending of proximal portion 142 from distal portion 144. For example, a grip can be formed on proximal end 134 of outer tray 102A or can be an extended flange with punched out finger holes.

FIG. 7 is a top plan view of an outer tray 102B having a grip 702 in accordance with one embodiment. FIG. 8 is a side plan view of outer tray 102B including grip 702 of FIG. 7 in accordance with one embodiment. FIG. 9 is a side plan view of outer tray 102B including grip 702 of FIG. 7 in a compact position in accordance with one embodiment. FIG. 10 is a perspective view of grip 702 of FIG. 7 in accordance with one embodiment.

Referring now to FIGS. 7, 8, 9, and 10 together, grip 702 includes a handle 704, a first handle bar extension 706, and a second handle bar extension 708. Handle bar extensions 706, 708 couple handle 704 to proximal portion 142 of tray 102B. Handle bar extensions 706, 708 project proximally from proximal portion 142. Handle 704 extends perpendicularly between handle bar extensions 706, 708.

Handle 704 and handle bar extensions 706, 708 define a grip opening 710 of grip 702. Handle 704 includes distally projecting finger features 712 projecting into grip opening 710. Finger features 712 are features to wrap fingers of the circulating nurse or other user around to facilitate grasping of handle 704.

To reduce the size, e.g., for shipping, grip 702 can be bent downward to be substantially parallel and adjacent to proximal end 134 of outer tray 102B as illustrated in FIG. 9. For example, grip 702 is bent downward and loaded into a shipping carton, e.g., a box.

FIG. 11 is a perspective view of a grip 702A of an outer tray of a catheter delivery system package in accordance with another embodiment. Grip 702A of FIG. 11 is similar to grip 702 of FIG. 10 and only the significant differences are discussed below.

Referring now to FIG. 11, in accordance with this embodiment, grip 702A includes finger features 712A including finger feature protrusions 1114. Finger feature protrusions 1114 project upward and outward from the plane of grip 702A. Finger feature protrusions 1114 are individual protrusions such that the circulating nurse or other user can pass their fingers between finger feature protrusions 1114 to facilitate grasping of handle 704A of grip 702A.

FIG. 12 is a perspective view of a grip 702B of an outer tray of a catheter delivery system package in accordance with yet another embodiment. Grip 702B of FIG. 12 is similar to grip 702 of FIG. 10 and only the significant differences are discussed below.

Referring now to FIG. 12, in accordance with this embodiment, grip 702A includes a handle 704B having a single larger handle protrusion 1216. Handle protrusion 1216 projects upward and outward from the plane of grip 702B. Handle protrusion 1216 protrudes such that the circulating nurse or other user can grasp handle protrusion 1216 to facilitate grasping of handle 704B of grip 702B.

This disclosure provides exemplary embodiments. The scope is not limited by these exemplary embodiments. Numerous variations, whether explicitly provided for by the specification or implied by the specification or not, such as variations in structure, dimension, type of material and manufacturing process may be implemented by one of skill in the art in view of this disclosure.

What is claimed is:

1. A packaging assembly comprising:
   an outer tray comprising:
   a proximal end;
   a distal end opposite the proximal end;
   a first side extending between the proximal end and the distal end;
   a second side opposite the first side and extending between the proximal end and the distal end, a single rectangular cavity being defined by the proximal end, the distal end, the first side, and the second side;
   a rigid proximal portion comprising a proximal section of the first side and a proximal section of the second side;
   a rigid distal portion comprising a distal section of the first side and a distal section of the second side; and
   a hinged portion coupling the proximal portion to the distal portion; and
   a continuous lid sealing flange extending across the proximal portion, the hinged portion, and the distal portion, wherein the hinged portion is configured to bend to move the proximal portion in a direction away from the lid sealing flange, wherein the proximal portion, the distal portion, the hinged portion and the lid sealing flange are integral.

2. The packaging assembly of claim 1 wherein the hinged portion comprises a plurality of corrugations.

3. The packaging assembly of claim 2 wherein the plurality of corrugations comprise an alternating series of ridges and furrows.

4. The packaging assembly of claim 3 wherein the alternating series of ridges and furrows are parallel to one another.

5. The packaging assembly of claim 2 wherein the plurality of corrugations are triangular shaped.

6. The packaging assembly of claim 1 wherein the hinged portion is flexible.

7. The packaging assembly of claim 1 further comprising a grip.

8. The packaging assembly of claim 7 wherein the proximal portion further comprises:
   a bottom surface;
   the first side extending from the bottom surface to the lid sealing flange; and
   the second side extending from the bottom surface to the lid sealing flange, wherein the grip is formed in the first and second sides.

9. The packaging assembly of claim 7 wherein the grip extends proximally from the proximal portion.

10. The packaging assembly of claim 9 wherein the grip comprises:
    a handle;
    a first handle bar extension coupling the handle to the proximal portion; and
    a second handle bar extension coupling the handle to the proximal portion, wherein the handle, the first handle bar extension, and the second handle bar extension define a grip opening of the grip.

11. The packaging assembly of claim 10 wherein the handle comprises finger features.

12. The packaging assembly of claim 11 wherein the finger features comprise finger feature protrusions.

13. The packaging assembly of claim 10 wherein the handle comprises a handle protrusion.

14. A packaging assembly comprising:
    an outer tray comprising:
    a rigid proximal portion;
    a rigid distal portion;
    a hinged portion coupling the proximal portion to the distal portion; and
    a continuous lid sealing flange;
    a lid coupled to the lid sealing flange of the outer tray, wherein the lid and the outer tray define a single rectangular sterile cavity therein; and
    an inner tray within the sterile cavity, the inner tray comprising a proximal portion within the proximal portion of the outer tray and a distal portion within the distal portion of the outer tray.

15. The packaging assembly of claim 14 further comprising a delivery system contained within the inner tray.

16. The packaging assembly of claim 14 wherein the hinged portion comprises a plurality of corrugations.

17. A method comprising:
   providing an inner tray within a single rectangular sealed cavity defined by an outer tray and a lid coupled to the outer tray, the outer tray comprising a continuous lid sealing flange, the lid being coupled to the lid sealing flange;
   removing at least a portion of the lid from the outer tray to expose a proximal portion of the inner tray; and
   bending a rigid proximal portion of the outer tray from a rigid distal portion of the outer tray to separate the proximal portion of the outer tray from the proximal portion of the inner tray.

18. The method of claim 17 wherein the bending comprises deforming a hinged portion of the outer tray, the hinged portion coupling the proximal portion of the outer tray to the distal portion of the outer tray.

19. The method of claim 17 further comprising removing the inner tray from the outer tray.

20. The method of claim 19 wherein the removing comprises removing a distal portion of the inner tray from the distal portion of the outer tray.

* * * * *